(12) United States Patent
Jimenez et al.

(10) Patent No.: US 8,170,681 B2
(45) Date of Patent: May 1, 2012

(54) METHOD OF CHARGING AN IMPLANTABLE MEDICAL DEVICE

(75) Inventors: Oscar Jimenez, Coral Gables, FL (US);
Guillermo Echarri, Miami, FL (US);
John E. Kast, Hugo, MN (US); James E. Riekels, New Hope, MN (US); Mark E. Schommer, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1163 days.

(21) Appl. No.: 10/998,486

(22) Filed: Nov. 29, 2004

(65) Prior Publication Data
US 2005/0113889 A1    May 26, 2005

Related U.S. Application Data

(62) Division of application No. 09/596,402, filed on Jun. 16, 2000, now Pat. No. 6,850,803.

(51) Int. Cl.
*A61N 1/40* (2006.01)
(52) U.S. Cl. .............. 607/61; 607/60; 607/32; 607/33
(58) Field of Classification Search .................. 607/61, 607/33, 36, 32, 60
See application file for complete search history.

(56) References Cited

U.S. PATENT DOCUMENTS

| | | | |
|---|---|---|---|
| 3,357,434 A | 12/1967 | Abel | |
| 3,888,260 A | 6/1975 | Fischell | |
| 4,041,955 A | 8/1977 | Kelly et al. | |
| 4,071,032 A | 1/1978 | Schulman | |
| 4,134,408 A | 1/1979 | Brownlee et al. | |
| 4,186,749 A | 2/1980 | Fryer | |
| 5,279,292 A | 1/1994 | Baumann et al. | |
| 5,314,457 A | 5/1994 | Jeutter et al. | |
| 5,380,321 A | 1/1995 | Yoon | |
| 5,401,272 A | 3/1995 | Perkins | |
| 5,411,537 A | 5/1995 | Munshi et al. | |
| 5,527,348 A | 6/1996 | Winkler et al. | |
| 5,562,714 A | 10/1996 | Grevious | |

(Continued)

FOREIGN PATENT DOCUMENTS
EP    0 499 939 A1    2/1992
(Continued)

OTHER PUBLICATIONS

International Search Report mailed Dec. 14, 2001 for International Appl. No. PCT/US01/18926.

(Continued)

*Primary Examiner* — Niketa Patel
*Assistant Examiner* — Joseph Stoklosa
(74) *Attorney, Agent, or Firm* — IPLM Group, P.A.

(57) ABSTRACT

A rechargeable implantable medical device with a magnetic shield placed on the distal side of a secondary recharging coil to improve charging efficiency is disclosed. The rechargeable implantable medical device can be a wide variety of medical devices such as neuro stimulators, drug delivery pumps, pacemakers, defibrillators, diagnostic recorders, cochlear implants. The implantable medical device has a secondary recharging coil carried over a magnetic shield and coupled to electronics and a rechargeable power source carried inside the housing. The electronics are configured to perform a medical therapy. Additionally a method for enhancing electromagnetic coupling during recharging of an implantable medical device is disclosed, and a method for reducing temperature rise during recharging of an implantable medical device is disclosed.

12 Claims, 15 Drawing Sheets

U.S. PATENT DOCUMENTS

| | | | |
|---|---|---|---|
| 5,613,935 A | 3/1997 | Jarvik | |
| 5,690,693 A | 11/1997 | Wang et al. | |
| 5,702,430 A * | 12/1997 | Larson et al. | 607/61 |
| 5,713,939 A | 2/1998 | Nedungadi et al. | |
| 5,733,313 A | 3/1998 | Barreras, Sr. et al. | |
| 5,741,316 A * | 4/1998 | Chen et al. | 607/61 |
| 5,749,912 A | 5/1998 | Zhang et al. | |
| 5,861,019 A | 1/1999 | Sun et al. | |
| 5,945,762 A | 8/1999 | Chen et al. | |
| 6,154,677 A | 11/2000 | Leysieffer | |
| 6,178,353 B1 | 1/2001 | Griffith et al. | |
| 6,275,737 B1 * | 8/2001 | Mann | 607/61 |
| 6,308,101 B1 | 10/2001 | Faltys et al. | |
| 6,324,431 B1 * | 11/2001 | Zarinetchi et al. | 607/61 |
| 6,327,504 B1 * | 12/2001 | Dolgin et al. | 607/61 |
| 6,389,318 B1 | 5/2002 | Zarinetchi et al. | |
| 6,496,733 B2 | 12/2002 | Zarinetchi et al. | |
| 6,505,077 B1 | 1/2003 | Kast et al. | |
| 6,516,227 B1 | 2/2003 | Meadows et al. | |
| 2002/0177884 A1 | 11/2002 | Ahn et al. | |

FOREIGN PATENT DOCUMENTS

| | | |
|---|---|---|
| EP | 0 499 939 B1 | 2/1992 |
| EP | 0 811 395 A2 | 12/1997 |
| EP | 0 811 395 A3 | 12/1997 |
| EP | 1 048 324 A2 | 11/2000 |
| WO | WO 98/37926 | 9/1998 |
| WO | WO 99/06108 | 2/1999 |
| WO | WO 99/44684 | 9/1999 |
| WO | WO 00/01442 | 1/2000 |
| WO | WO 01/83029 A1 | 11/2001 |
| WO | WO 01/97908 A2 | 12/2001 |
| WO | WO 01/97908 A3 | 12/2001 |

OTHER PUBLICATIONS

Medtronic, Inc. "Implantable Neurostimulation Systems", 1998.

"The Heart," Popular Science, Jan. 2000.

* cited by examiner

METHOD OF CHARGING AN IMPLANTABLE MEDICAL DEVICE

RELATED APPLICATIONS

This application is a divisional of and claims priority from U.S. application Ser. No. 09/596,402, "IMPLANTABLE MEDICAL DEVICE WITH EXTERNAL RECHARGE COIL," filed Jun. 16, 2000, the contents of which are hereby incorporated herein by reference.

This application is related to a continuation application of the above-identified application entitled "IMPLANTABLE MEDICAL DEVICE AND ELECTRICAL STIMULATION DEVICE WITH MAGNETIC SHIELD," filed on even date herewith.

FIELD OF THE INVENTION

This disclosure relates to an implantable medical device and more specifically a rechargeable implantable medical device that produces a medical therapy.

BACKGROUND OF THE INVENTION

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. Examples of implantable medical devices include neuro stimulators, drug delivery pumps, pacemakers, defibrillators, diagnostic recorders, and cochlear implants. Some implantable medical devices provide therapies with significant power demands. To reduce the size of the power source and to extend the life of the power source, some of these implantable devices can be recharged while implanted with a transcutaneous recharge signal produced by a primary coil.

Implantable medical devices configured for recharging are typically configured with either the recharging coil internal to the medical device housing, external to the housing, or remotely located away from the housing. However the medical device recharging coil is configured, it is desirable to improve recharging efficiency for benefits such as decreased recharging time and decreased medical device temperature rise while recharging.

For the foregoing reasons there is a need for a rechargeable implantable medical device with improved recharging efficiency.

BRIEF SUMMARY OF THE INVENTION

Improved recharging efficiency for a rechargeable implantable medical device is accomplished with a magnetic shield placed on the secondary recharging coil distal side. The secondary recharging coil is coupled to electronics and a rechargeable power source carried inside the housing. The electronics are configured to perform a medical therapy. In one embodiment, an external secondary recharging coil is carried on the housing exterior, and the magnetic shield is placed between the recharging coil distal side and the housing proximal side. In another embodiment, a remote secondary recharging coil is placed away from the housing, and the magnetic shield is placed on the distal side of the secondary recharging coil. In another embodiment, secondary recharging coil is internal, and the magnetic shield is placed on the distal side of the secondary recharging coil between the secondary recharging coil and the electronics.

In a preferred embodiment, the present invention provides a method having the steps of operatively coupling a secondary charging coil to an implantable medical device, positioning a magnetic shield between the secondary charging coil and the implantable medical device, and coupling electromagnetic flux from the primary charging coil from a side of the secondary charging coil opposite from the magnetic shield.

In another embodiment, the present invention provides a method of enhancing electromagnetic coupling of an implantable medical device recharging coil. A secondary recharging coil is positioned in operational relationship to an implantable medical device. A magnetic shield is positioned on a distal side of the secondary recharging coil. Electromagnetic flux lines are attracted from a primary recharging coil to the secondary recharging coil with the magnetic shield. Electromagnetic coupling is improved between a primary recharging coil and a secondary recharging coil. Efficiency of energy transfer from the primary recharging coil to the secondary recharging coil is improved.

In another embodiment, the present invention provides a method of reducing temperature rise during recharging of an implantable medical device external recharging coil. A secondary recharging coil is positioned in operational relationship to an implantable medical device. A magnetic shield is positioned on a distal side of the secondary recharging coil; reducing electromagnetic flux lines that couple with the housing. Eddy currents in the housing caused by electromagnetic flux lines that couple with the housing are reduced. Temperature rise during recharging are reduced because of reduced eddy currents in the housing.

In another embodiment, the present invention provides a method of electromagnetic coupling a primary charging coil with a secondary charging coil of an implantable medical device. The secondary charging coil is operatively coupled to the implantable medical device. A magnetic shield is positioned between the secondary charging coil the implantable medical device. The primary coil is electromagnetically coupled with the secondary coil from a side of the secondary coil opposite from the magnetic shield.

In a preferred embodiment, electromagnetic coupling between the primary charging coil and the secondary charging coil is enhanced.

In a preferred embodiment, the enhanced electromagnetic coupling is greater than 10 percent coupling efficiency at about one centimeter separation between the primary charging coil and the secondary charging coil.

In a preferred embodiment, efficiency of energy transfer from the primary charging coil to the secondary charging coil is improved.

In a preferred embodiment, charging efficiency between the primary charging coil and the secondary charging coil is improved.

In a preferred embodiment, the secondary recharging coil is carried on the proximal face of the housing.

In a preferred embodiment, the secondary recharging coil is an external secondary recharging coil located away from a housing of the implantable medical device.

In another embodiment, the present invention provides a method of charging of an implantable medical device with an external charging coil. A secondary charging coil is operatively coupled to the implantable medical device. A magnetic shield is positioned between the secondary charging coil and the implantable medical device. Electromagnetic flux from the primary charging coil is applied from a side of the secondary charging coil opposite from the magnetic shield.

In a preferred embodiment, the applying step results in reduced electromagnetic flux lines that couple with a housing of the implantable medical device.

In a preferred embodiment, the applying step results in reduced eddy currents in the housing of the implantable medical device caused by electromagnetic flux lines that couple with the housing.

In a preferred embodiment, a temperature rise induced through eddy currents in the housing during charging is reduced.

In a preferred embodiment, charging efficiency is improved by decreasing flux lines that couple with the housing.

In a preferred embodiment, charging efficiency is improved through reduced eddy currents in the housing.

In a preferred embodiment, reduced eddy currents during recharging also reduces medical device temperature rise during charging.

In a preferred embodiment, the temperature rise of the implantable medical device during charging is less than two degrees Celsius.

In a preferred embodiment, the magnetic shield is a material with high magnetic permeability.

In a preferred embodiment, the method further comprises the step of selecting the magnetic shield from the group consisting of: amorphous metal film, amorphous metal wire, and magnetic alloy.

In a preferred embodiment, the medical device is selected from the group consisting of: neuro stimulators, pacemakers, defibrillators, drug delivery pumps, diagnostic recorders, and cochlear implants.

DETAILED DESCRIPTION OF THE INVENTION

Figure 1:
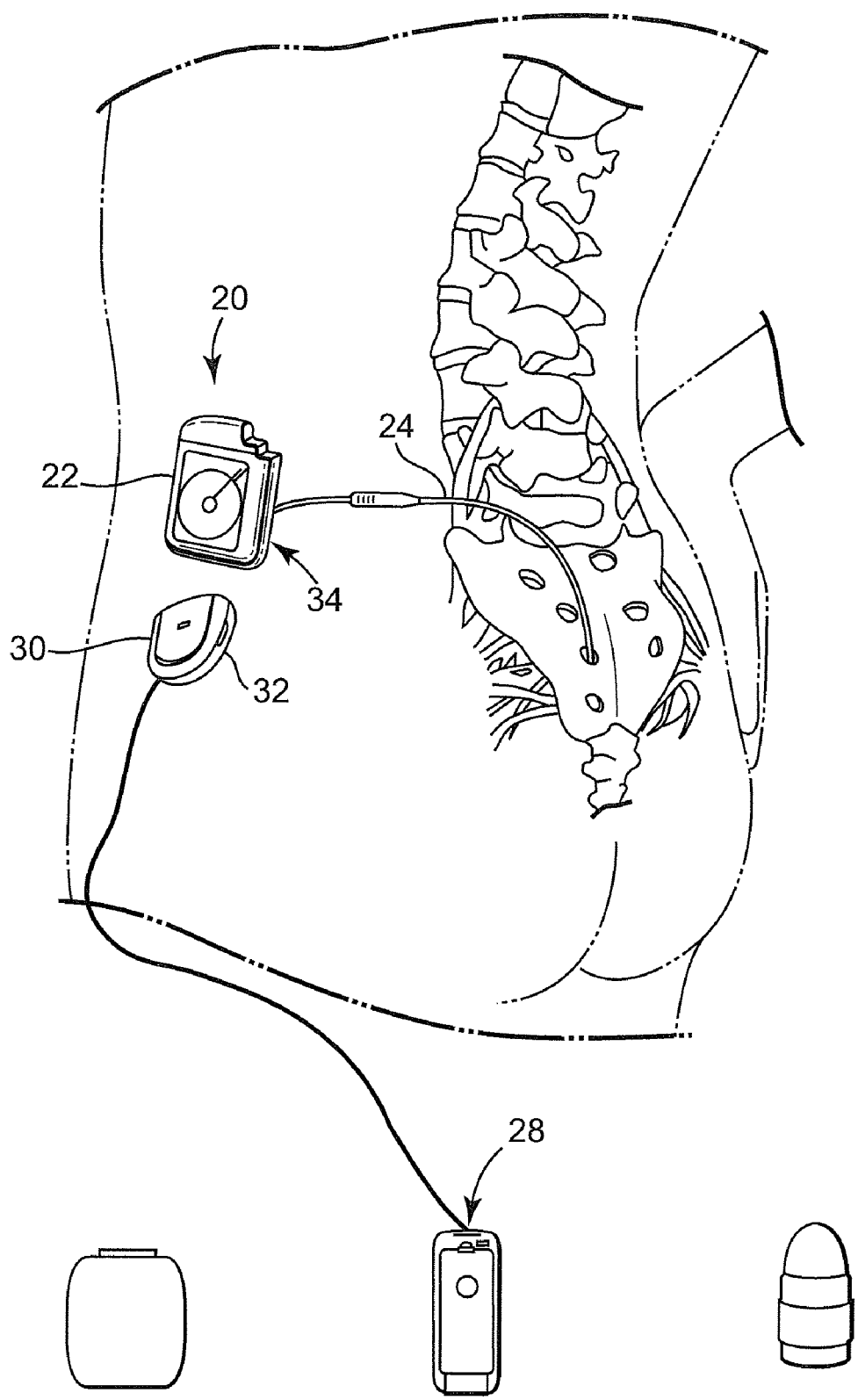
FIG. 1 shows an environment of a rechargeable implantable medical device.

FIG. 1 shows the general environment of one rechargeable implantable medical device 20 embodiment. An implantable neuro stimulator 22 is shown in FIG. 1, but other embodiments such as drug delivery pumps, pacemakers, defibrillators, diagnostic recorders, cochlear implants, and the like are also applicable. Implantable medical devices 20 are often implanted subcutaneously approximately one centimeter below the surface of the skin with an electrical lead 24 or catheter extending to one or more therapy sites. The rechargeable implantable medical device 20 is recharged with a recharging device 28 such as a patient charger or programmer that also has a charging capability.

Recharging an implanted medical device 20 generally begins with placing a recharging head 30 containing a primary recharging coil 32 against the patient's skin near the proximal side of the medical device 20. Some rechargers 28 have an antenna locator that indicates when the recharge head 30 is aligned closely enough with the implanted medical device 20 for adequate inductive charge coupling. The recharge power transfer signal is typically a frequency that will penetrate transcutaneous to the location of the implanted medical device 20 such as a frequency in the range from 5.0 KHz to 10.0 KHz. The power transfer signal is converted by the implantable medical device 20 into regulated DC power that is used to charge a rechargeable power source 34. Telemetry can also be conducted between the recharger 28 and the implanted medical device 20 during recharging. Telemetry can be used to aid in aligning the recharger 28 with the implanted medical device 20, and telemetry can be used to manage the recharging process. Telemetry is typically conducted at a frequency in the range 150 KHz to 200 KHz using a medical device telemetry protocol. For telemetry, the recharger 28 and implanted medical device 20 typically have a separate telemetry coil. Although, the recharging coil can be multiplexed to also serve as a telemetry coil.

Figure 2:
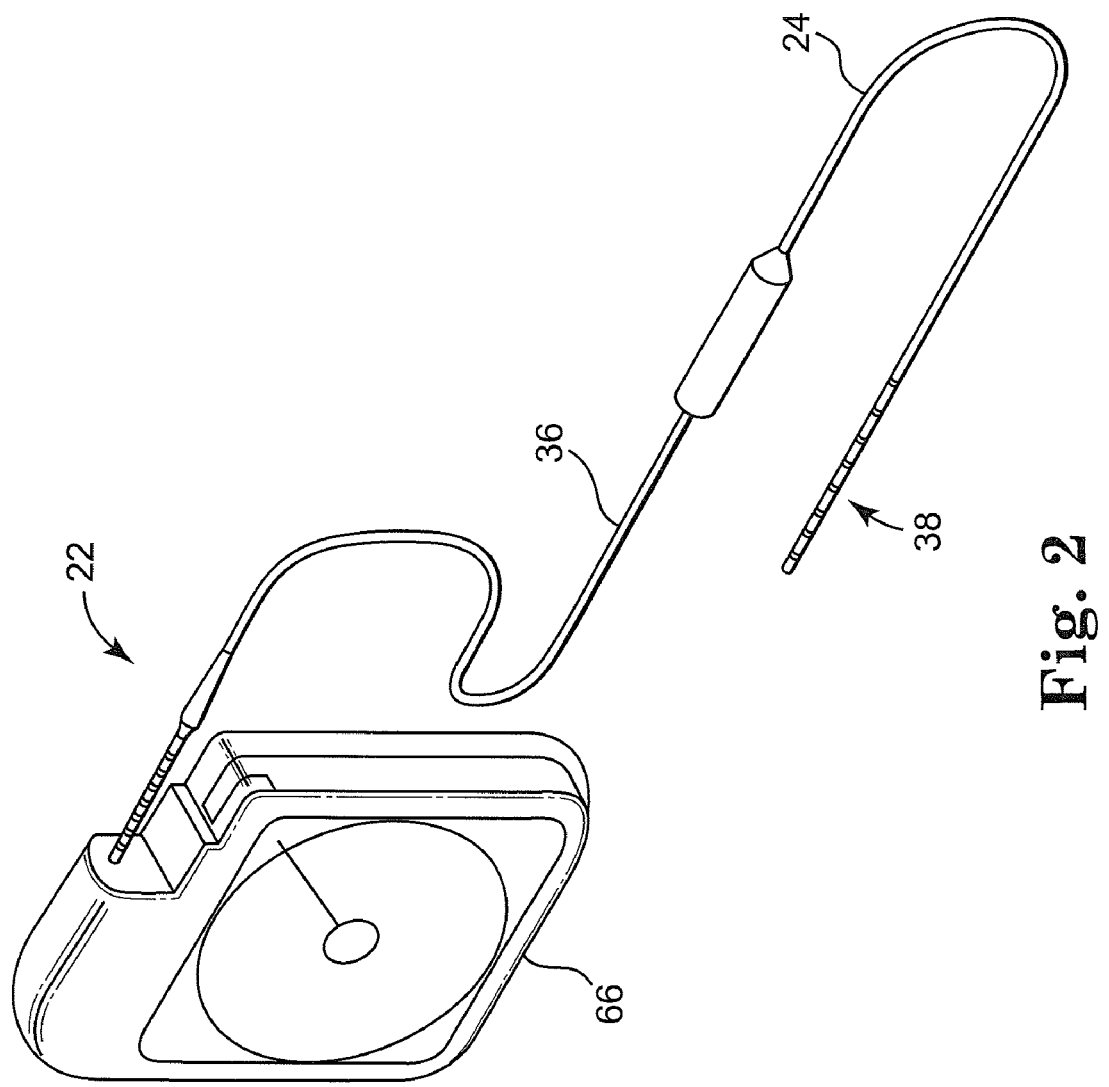
FIG. 2 shows a rechargeable implantable medical device neuro stimulator embodiment.
Figure 3:
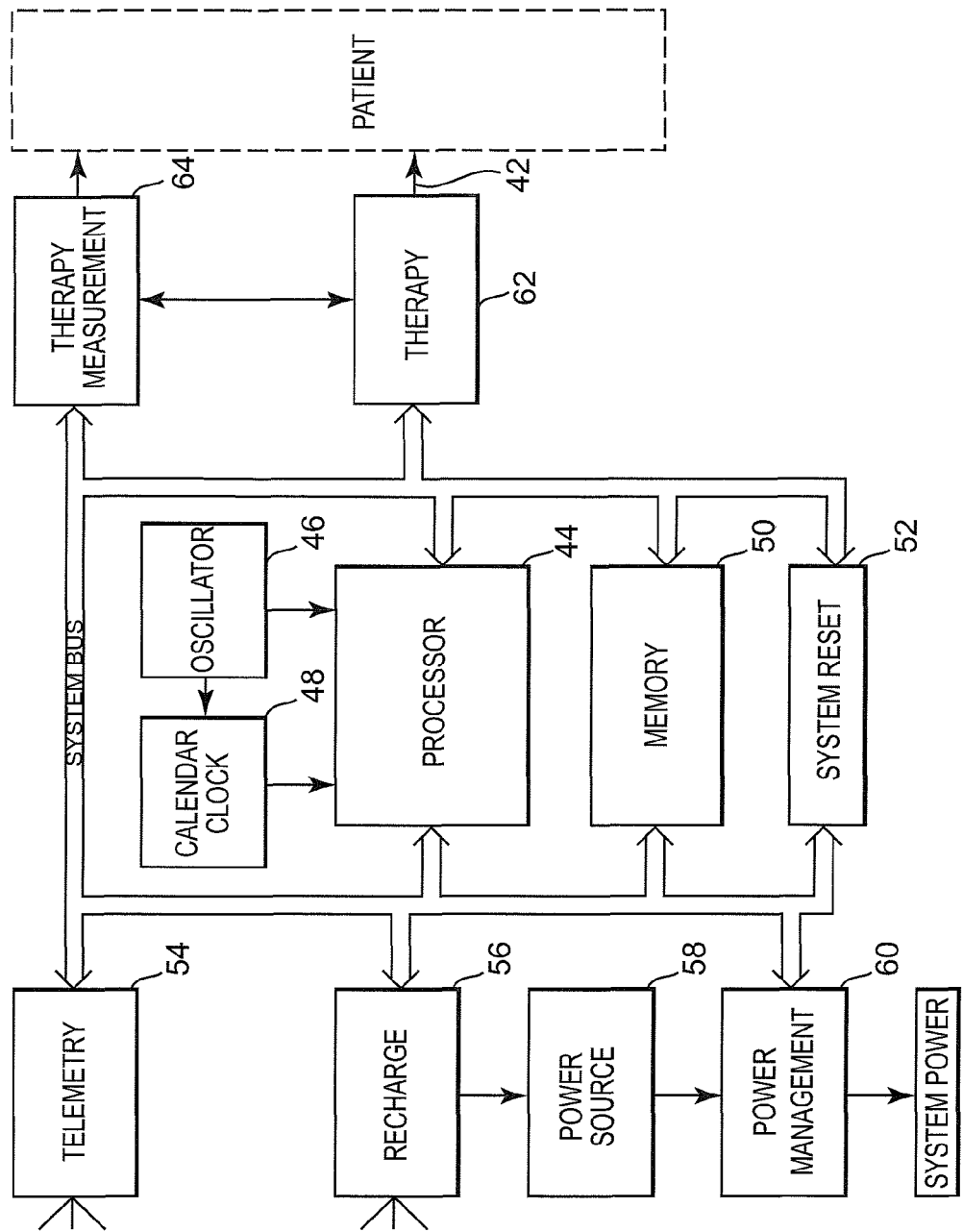
FIG. 3 shows a neuro stimulator electronics block diagram embodiment.

FIG. 2 shows a rechargeable neuro stimulator 22 with a lead extension 36 and a lead 24 having electrical contacts 38 embodiment. FIG. 3 shows a neuro stimulator electronics 40 block diagram embodiment. The neuro stimulator 22 generates a programmable electrical stimulation signal. The neuro stimulator electronics 40 comprises a processor 44 with an oscillator 46, a calendar clock 48, memory 50, and system reset 52, a telemetry module 54, a recharge module 56, a power source 58, a power management module 60, a therapy module 62, and a therapy measurement module 64. All components of the neuro stimulator 22 are contained within or carried on the housing 66.

Figure 4A:
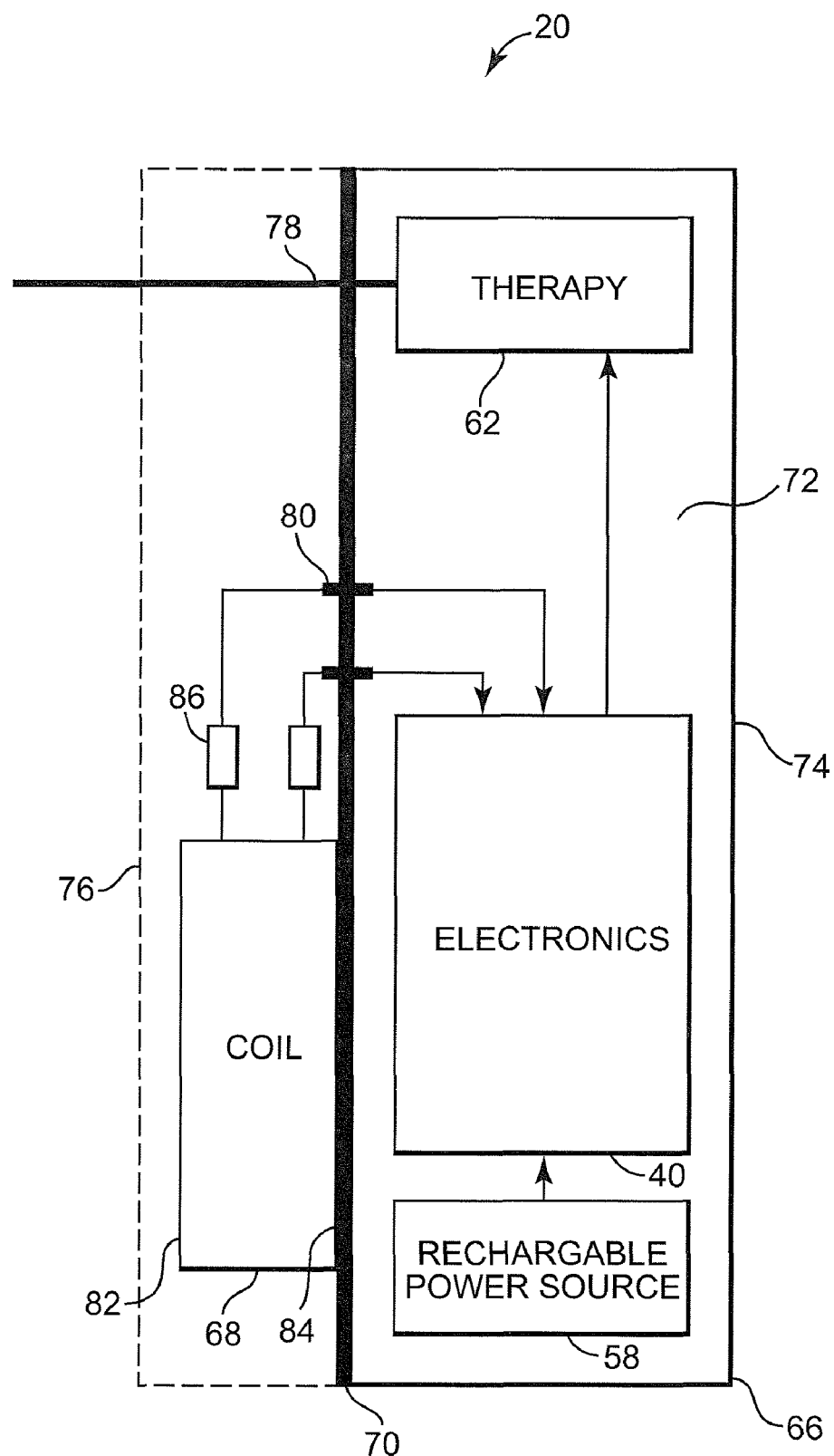
FIG. 4a shows a rechargeable implantable medical device with external secondary recharging coil block diagram embodiment.
Figure 4B:
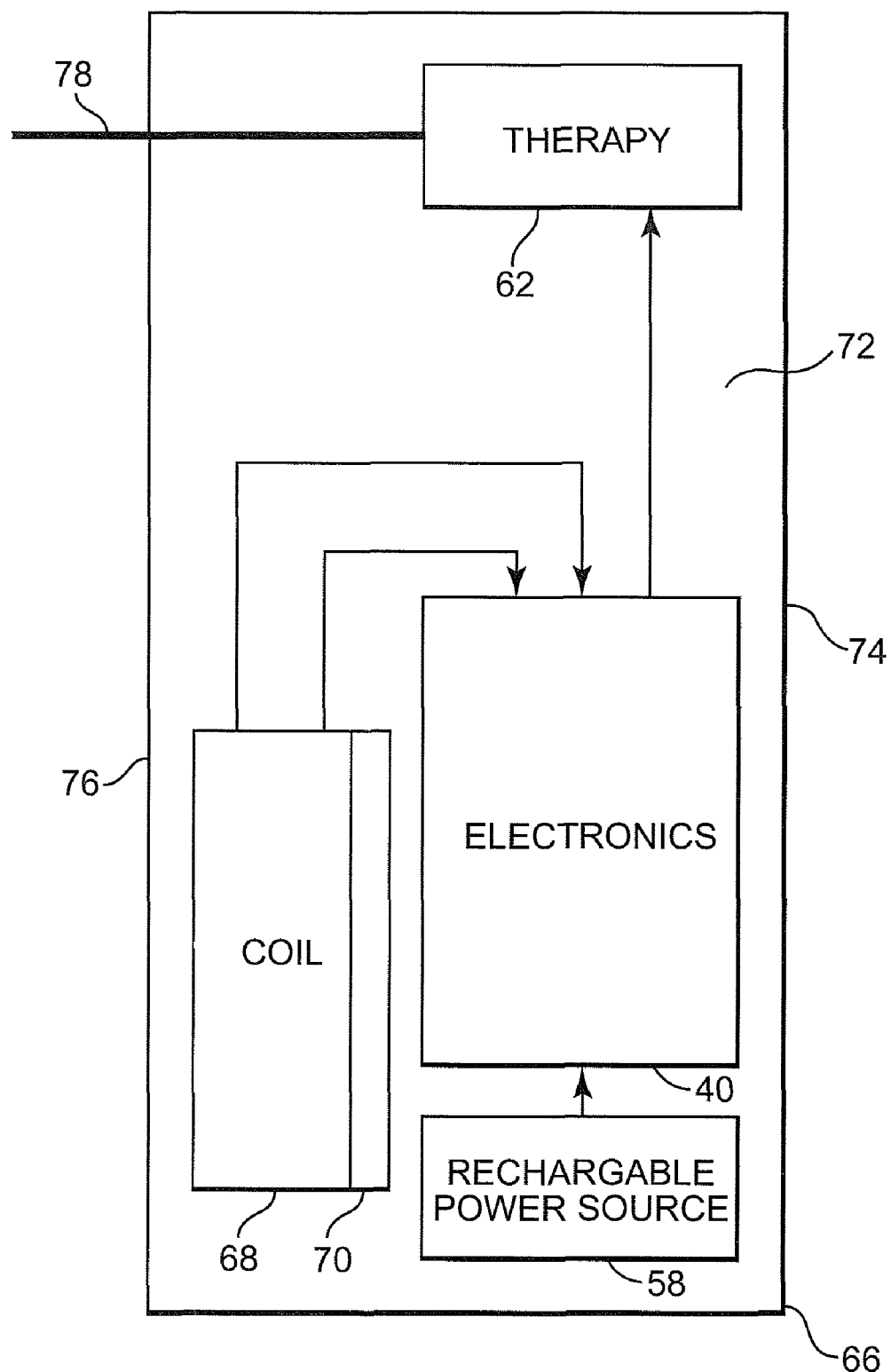
FIG. 4b shows rechargeable implantable medical device with remote external secondary recharging coil block diagram embodiment.
Figure 4C:
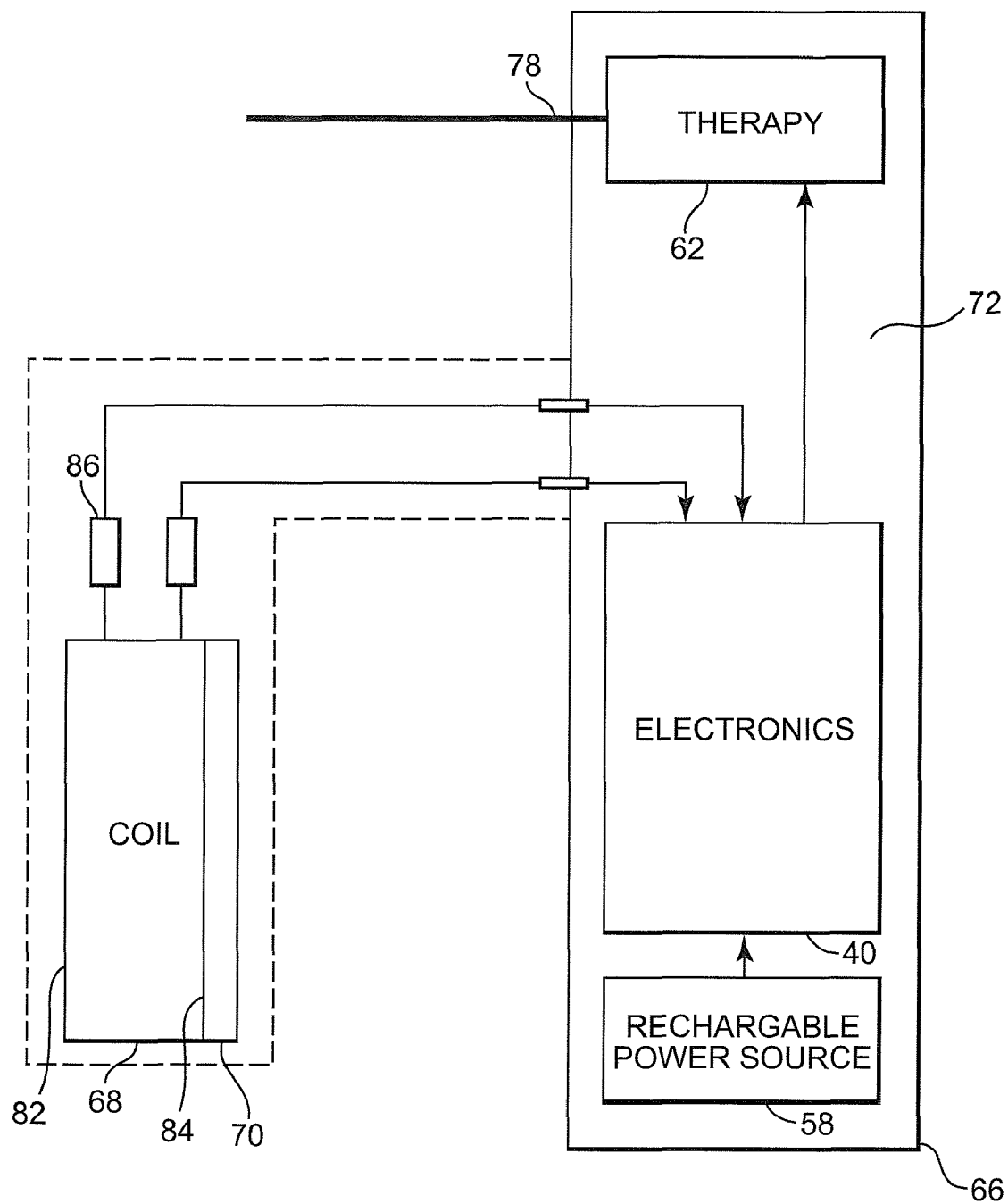
FIG. 4c shows rechargeable implantable medical device with internal secondary recharging coil block diagram embodiment.

FIGS. 4a-4c show an implantable medical device 20 with recharging coil block diagrams. The implantable medical device 20 with external recharging coil magnetic shield comprises a housing 66, electronics 40, a rechargeable power source 58, a secondary recharging coil 68, and a magnetic shield 70. The housing 66 has an interior cavity 72, an exterior surface 74, a proximal face 76, a therapy connection 78, and a recharge feedthrough 80. The therapy connection 78 can be any type of therapy connection 78 such as a stimulation feedthrough, a drug infusion port, or a physiological sensor. There can also be more than one therapy connection 78 and a combination of different types of therapy connections 78. The housing 66 is hermetically sealed and manufactured from a biocompatible material such as titanium, epoxy, ceramic, and the like. The housing 66 contains electronics 40.

The electronics 40 are carried in the housing interior cavity 72 and configured to perform a medical therapy. The electronics 40 are electrically connected to both a therapy module therapy connection 78 and the recharge feedthrough 80. The rechargeable power source 58 is carried in the housing interior cavity 72 and coupled to the electronics 40. The rechargeable power source 58 can be a physical power source such as a spring, an electrical power source such as a capacitor, or a chemical power source such as a battery. The battery can be a hermetically sealed rechargeable battery such as a lithium ion (Li+) battery and the like. The electronics 40 are coupled to the secondary recharging coil 68.

The secondary recharging coil 68 is coupled to the electronics 40 and can also be coupled to the rechargeable power source 58 in addition to the electronics 40. In various embodiments the secondary recharging coil 68 can be located on the housing proximal face 76, inside the housing 66, and remotely away from the housing 66. The secondary recharging coil 68 has a proximal side 82 implanted toward a patient's skin and a distal side 84 implanted toward a patient's internal organs. The secondary recharging coil 68 is manufactured from a material with electromagnetic properties such as copper wire, copper magnet wire, copper litz woven wire, gold alloy or the like. The secondary recharging coil 68 can be manufactured from a wide variety of sizes such as wire diameters in the range from about 0.016 cm (34 AWG, American Wire Gauge) to about 0.040 cm (26 AWG), or any other suitable diameter. The secondary recharging coil 68 is coupled to the recharging feedthroughs 80 with an electrical connection 86. The electrical connection 86 is protected with a hermetic seal to prevent the electrical connection 86 from being exposed to biological tissue or fluids. The hermetic seal is a biocompatible material and can take many forms including potting material, polymer encapsulation, coil cover with polymer seal, or the like.

The embodiment in FIG. 4a has a secondary recharging coil 68 carried on the proximal face 76 of the implantable medical device 20 with the magnetic shield 70 positioned between the secondary recharging coil 68 and the proximal face 76. The external secondary recharging coil 68 increases recharge efficiency because the secondary recharging coil 68 is located just under the surface of the skin to decrease coupling distance, and the magnetic shield 70 is positioned to both attract flux lines to the area of the secondary recharging coil 68 and reduce flux lines from coupling into the housing 66 to reduce eddy currents in the housing 66. The embodiment in FIG. 4b has an internal secondary recharging coil 68 with the magnetic shield 70 positioned between the internal secondary recharging coil 68 and the electronics 40. The internal secondary recharging coil 68 reduces manufacturing complexity and the magnetic shield 70 improves coupling and reduces eddy currents induced into the electronics 70. The embodiment in FIG. 4c has a remote secondary recharging coil 68 located away from the housing 66 with the magnetic shield 70 positioned on the distal side of the secondary recharging coil 68. The remote secondary recharging coil 68 permits the clinician more positioning options while the magnetic shield 70 improves coupling.

Figure 5:
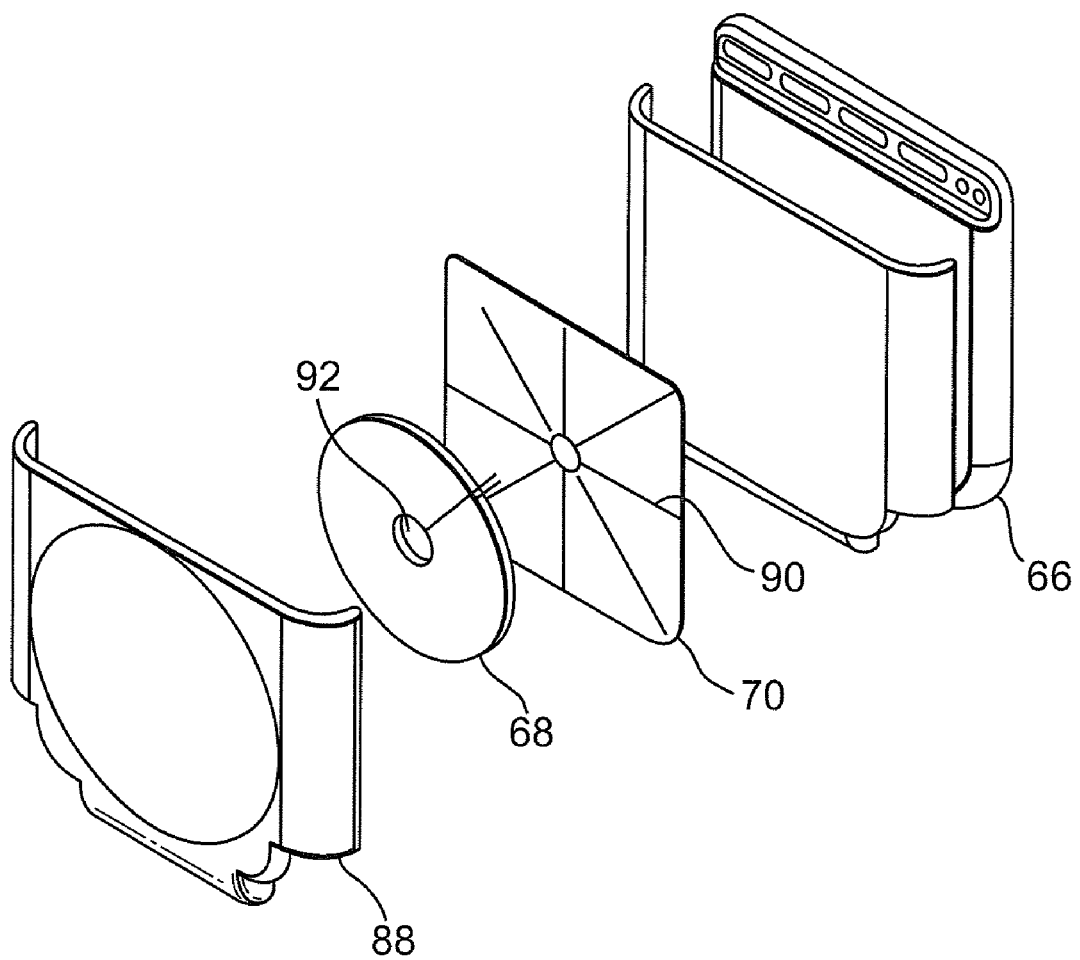
FIG. 5 shows an exploded view of a neuro stimulator embodiment.

FIG. 5 shows an embodiment of a neuro stimulator 22 with some external components exploded away from the housing 66. The external components include a coil cover 88, a secondary recharging coil 68, and a magnetic shield 70. The magnetic shield 70 is positioned between the secondary recharging coil 68 and the housing 66. The magnetic shield 70 is typically configured to cover at least the footprint of the secondary recharging coil 68 on the implantable medical device housing 66, and the magnetic shield 70 can be configured to cover the proximal face 76 of the medical device 20 or most or all of the implantable medical device 20. The magnetic shield 70 is manufactured from a material with high magnetic permeability such as amorphous metal film, amorphous metal fibers, a magnetic alloy, ferrite materials, and the like. Amorphous metal has a disordered atomic structure and some compositions such as Co—Fe—Si—B have high permeability and near zero magnetostriction. Commercially available materials that are suitable for a magnetic shield include Honeywell Metglass™ amorphous foil 2714A and Unitika Sency™ amorphous metal fiber. The magnetic shield 70 is configured with a thickness suitable for the application such as in the range from about 0.0254 centimeters (0.001 inch) to 0.0101 centimeters (0.004 inch) thick. The magnetic shield 70 can be configured with eddy cuts 90 to reduce perpendicular magnetic flux induced eddy current flow in the magnetic shield itself. Eddy cuts 90 can be configured with dimensions and placement suitable for the application such as with a width in the range from 0.0025 centimeters (0.001 inch) to 0.0508 centimeters (0.02 inch) in width configured in a radial pattern on the magnetic shield 70. The eddy cuts 90 can be formed with a variety of manufacturing processes such as laser cutting, die cutting, and chemical etching. The magnetic shield 70 can also be shaped to meet geometry requirements of the implantable medical device 20 such as with a central opening 92 to facilitate placement of the secondary recharge coil 68.

The magnetic shield 70 can be configured with more than one magnetic shield 70 positioned between the secondary recharge coil 68 and the implantable medical device housing 66 to reduce eddy currents induced by radial magnetic flux. Multiple magnetic shields 70 can be used to constrain eddy currents to an individual magnetic shield 70 or for other manufacturing reasons. To aid in constraining eddy currents to an individual magnetic shield 70, an insulator 94 can be placed between the magnetic shields 70. The insulator is a material with good electrical insulating properties such as plastic, mylar, polyimide, insulating tape, insulating adhesive, and the like.

Figure 6:
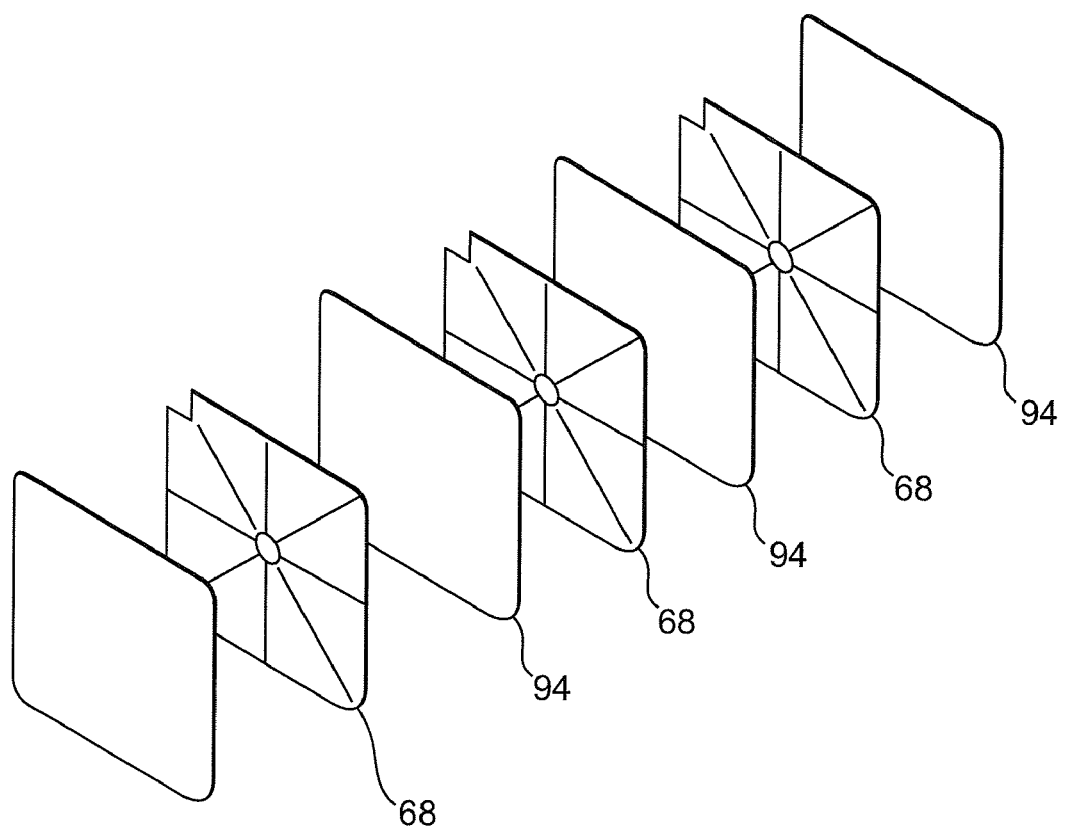
FIG. 6 shows an exploded view of a magnetic shield embodiment.
Figure 7:
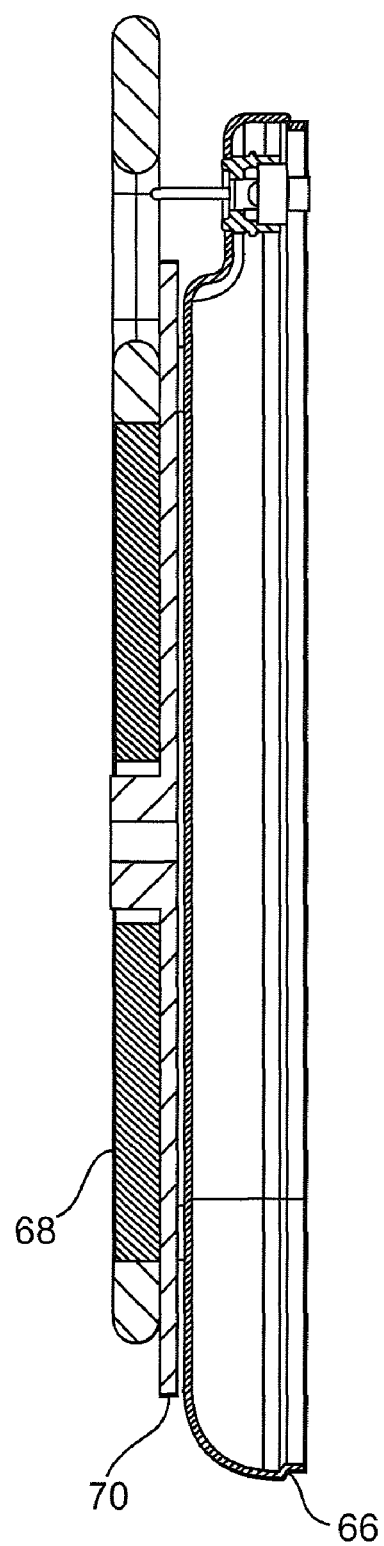
FIG. 7 shows a side view of a neuro stimulator embodiment.
Figure 8A:
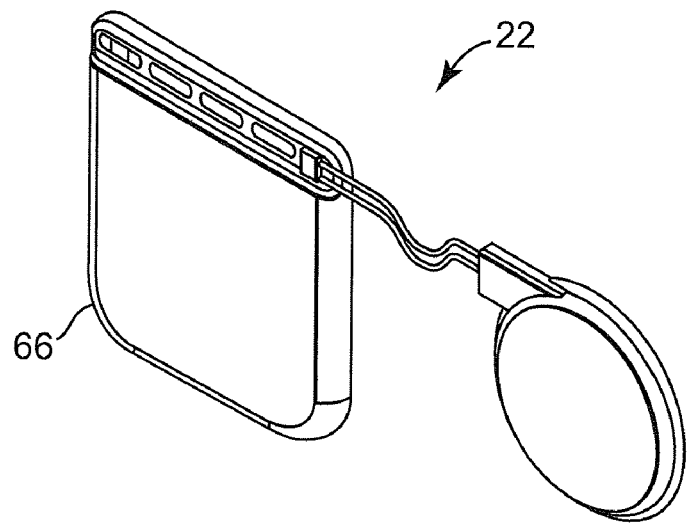
FIG. 8a shows a neuro stimulator with remote secondary recharging coil embodiment.
Figure 8B:
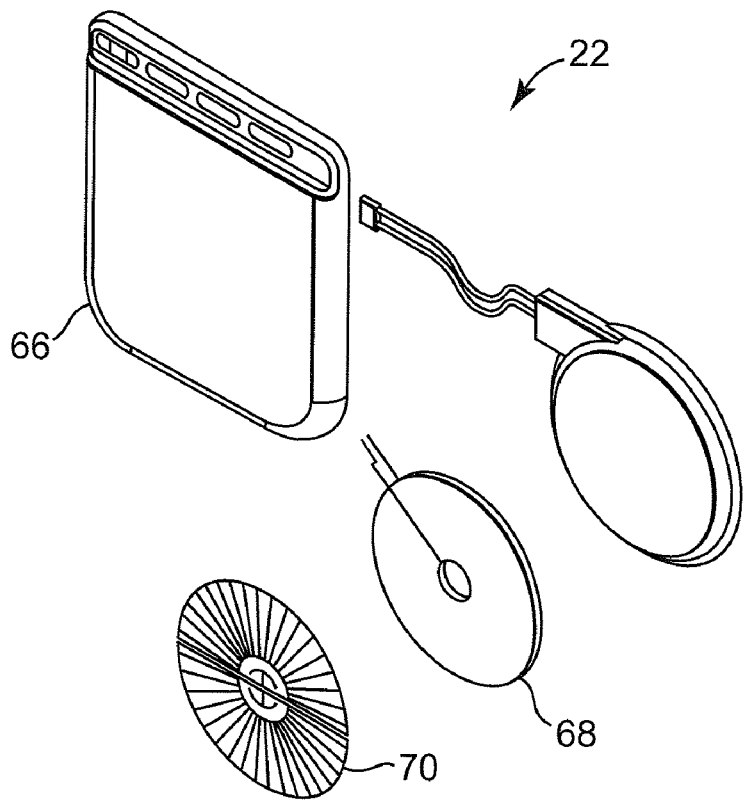
FIG. 8b shows an exploded view of the remote secondary recharging coil embodiment.

FIG. 6 shows a multiple magnetic shield 70 embodiment. An insulating sheet 94 separates the magnetic shields 70. Multiple magnetic shields 70 improve magnetic shielding while reducing the formation of eddy currents in the magnetic shield 70 itself. The insulating sheet 94 is a material with good insulating qualities suitable for placement between magnetic shields 70 such as plastic, mylar, polyimide, insulating tape, insulating adhesive, and the like. FIG. 7 shows a side view of a neuro stimulator 22 embodiment. FIG. 8a shows a neuro stimulator 22 with remote secondary recharging coil 68 embodiment, and FIG. 8b shows an exploded view of the remote secondary recharging coil 68 embodiment.

Figure 9A:
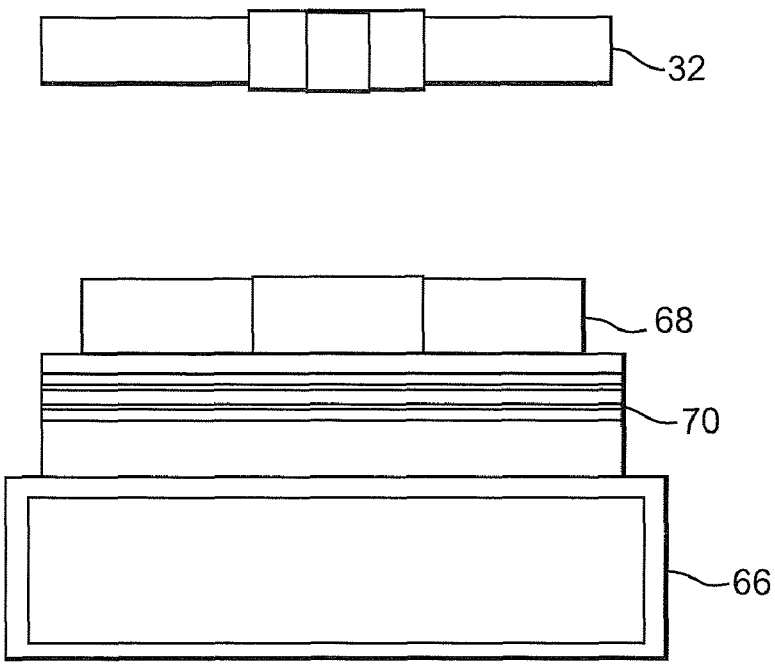
FIG. 9a shows a simulation test configuration with a magnetic shield under a secondary recharging coil.
Figure 9B:
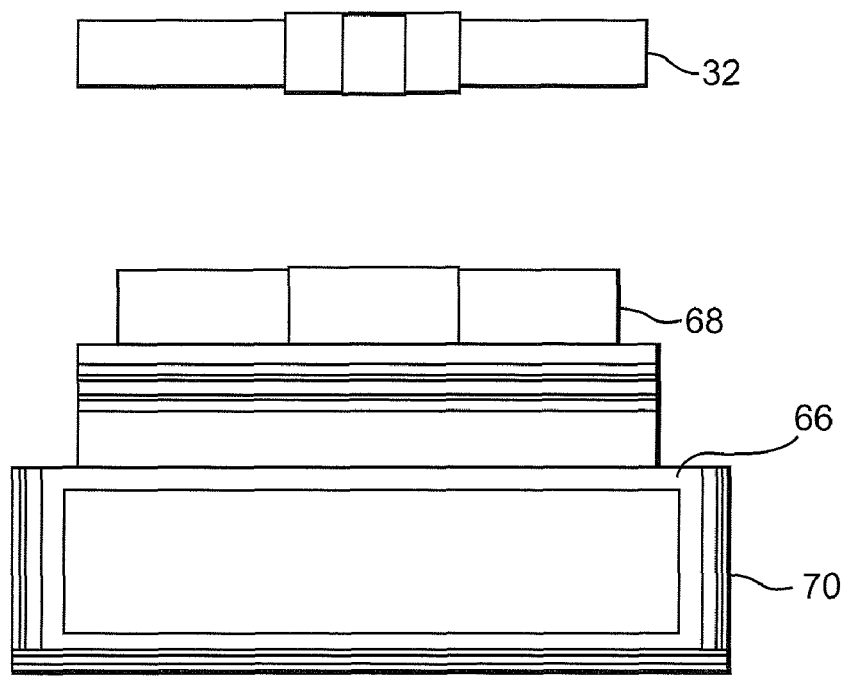
FIG. 9b shows a simulation test configuration with a magnetic covering the medical device housing.

FIG. 9a shows a simulation test configuration with a magnetic shield 70 under a secondary recharging coil 68, and FIG. 9b shows a simulation test configuration with a magnetic shield 70 covering the medical device housing 66. FIGS. 9a and 9b are not to scale. Both simulation test configurations were done using two dimensional finite element analysis magnetic modeling software such as that available from MagSoft™ located in Troy, N.Y. Also both simulation test configurations used the following parameters. The primary recharging coil 32 has 250 turns of 0.051 cm diameter (24 AWG) magnet wire with an outer diameter of 4.572 cm (1.8 inches) and an inner diameter of 2.019 cm (0.795 inches) with a Toroidal magnetic core in the center having an effective relative permeability $\mu_R$ of 10. The secondary recharging coil 68 has 200 turns of 0.025 cm diameter (30 AWG) magnet wire forming a coil with an outer diameter of 3.302 cm (1.30 inches) and an inner diameter of 0.635 cm (0.25 inch). The medical device housing 66 is titanium having a thickness of 0.030 cm (0.012 inch). The separation between the primary recharging coil 34 and the secondary recharging coil 68 is 1.0 cm (0.394 inch). The recharge power transfer signal is 150 VAC peak-to-peak at 8.0 KHz. The magnetic shield 70 in FIG. 9a is composed of alternating 0.002 cm thick layers of Metglass and air gap with the secondary recharging coil 68 located 0.013 cm (0.005 inch) above the magnetic shield 70. The magnetic shield 70 in FIG. 9b has the magnetic shield 70 described for FIG. 9a and in addition a similar magnetic shield 70 covering the medical device 20 sides and bottom.

Figure 10A:
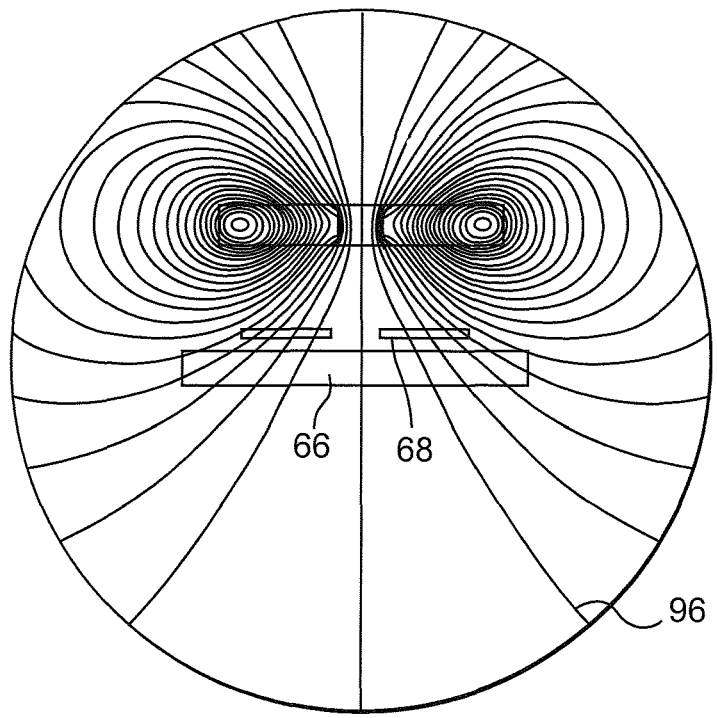
FIG. 10a shows simulation results without a magnetic shield of power transfer signal flux lines.

FIG. 10a shows simulation results without a magnetic shield 70 of power transfer signal flux lines 96 interacting with a secondary recharging coil 68 and a medical device housing 66. Power loss in the medical device housing 66 is 0.430 Watts and the coupling efficiency is 12.3%. For this simulation, the magnetic shield 70 shown in FIG. 9a was removed.

Figure 10B:
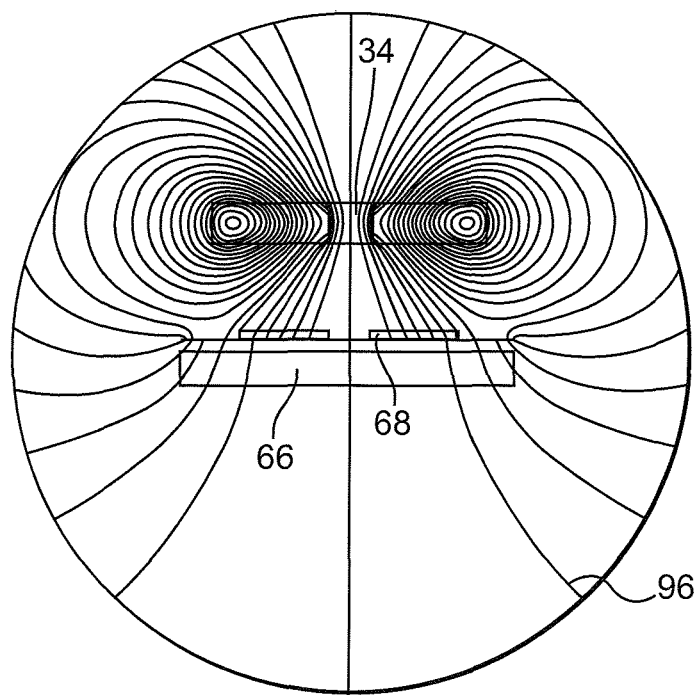
FIG. 10b shows simulation results with a magnetic shield under a secondary recharging coil of power transfer signal flux lines.

FIG. 10b shows simulation results with a magnetic shield 70 placed under the secondary recharging coil 68 and power transfer signal flux lines 96 interacting with the secondary recharging coil 68 and medical device housing 66. Power loss in the medical device housing is 0.143 Watts and the coupling efficiency is 25%. The simulation results show improved recharging efficiency through enhanced electromagnetic coupling between the secondary recharging coil 68 and a primary recharging coil 34. The improved electromagnetic coupling between the primary recharging coil 34 can be in the range from about 10% to 28% coupling at about one centimeter. Electromagnetic coupling efficiency is calculated with the following equation:

Coupling Efficiency=Pout/Pin×100% where Pout is measured at the secondary recharging coil 68 and Pin is measured at the primary recharging coil 34. The recharging efficiency is also improved through reduced eddy currents in the housing 66. Reducing eddy currents during recharging also reduces medical device 22 temperature rise during recharging for improved safety.

Figure 10C:
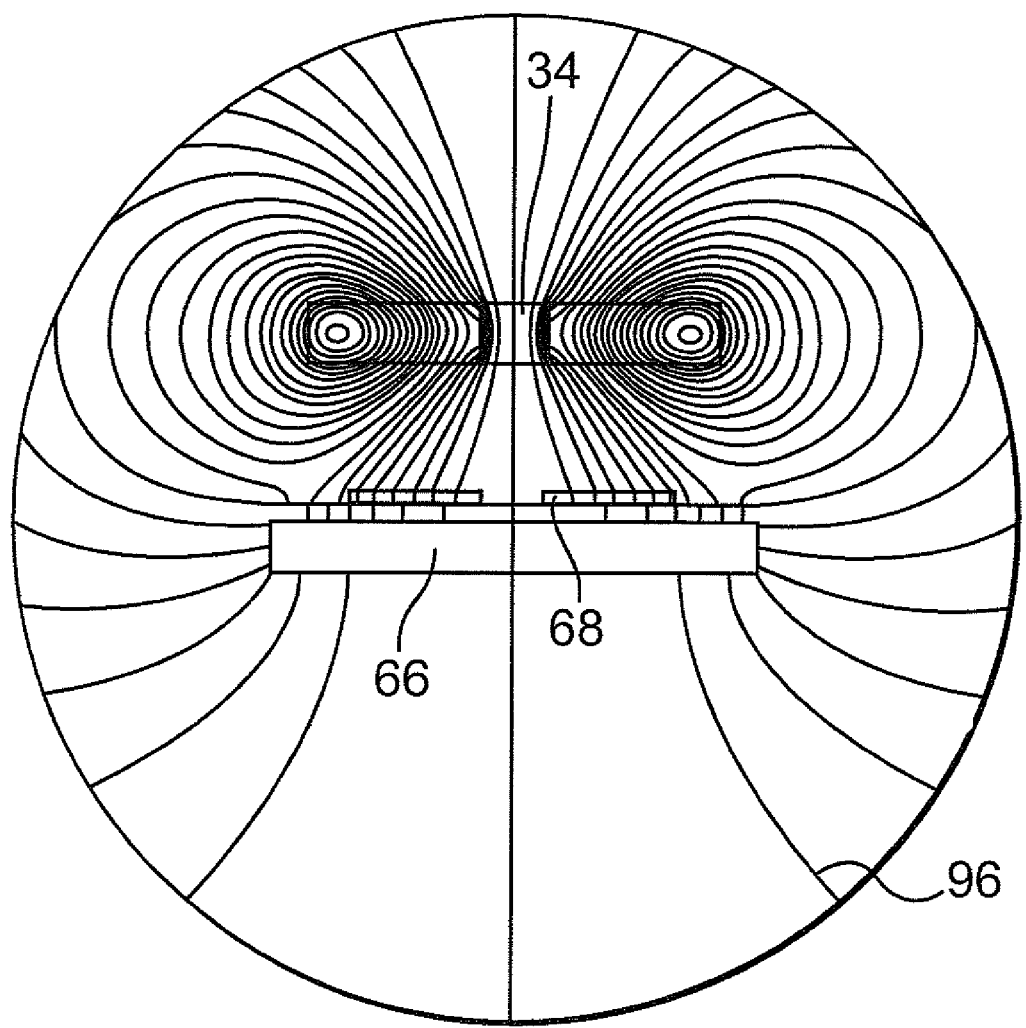
FIG. 10c shows simulation results with a magnetic shield covering the medical device housing of power transfer signal flux lines.

FIG. 10c shows simulation results with a magnetic shield 70 covering the medical device housing 66. Power loss in the medical device housing 66 is 0.38 mWatts and the coupling efficiency is 27.5%. The simulation results show improved recharging efficiency over the simulation in FIG. 10b. The recharging efficiency is also improved through reduced eddy currents in the housing 66. Reducing eddy currents during recharging also reduces medical device 20 temperature rise during recharging for improved safety.

Figure 11:
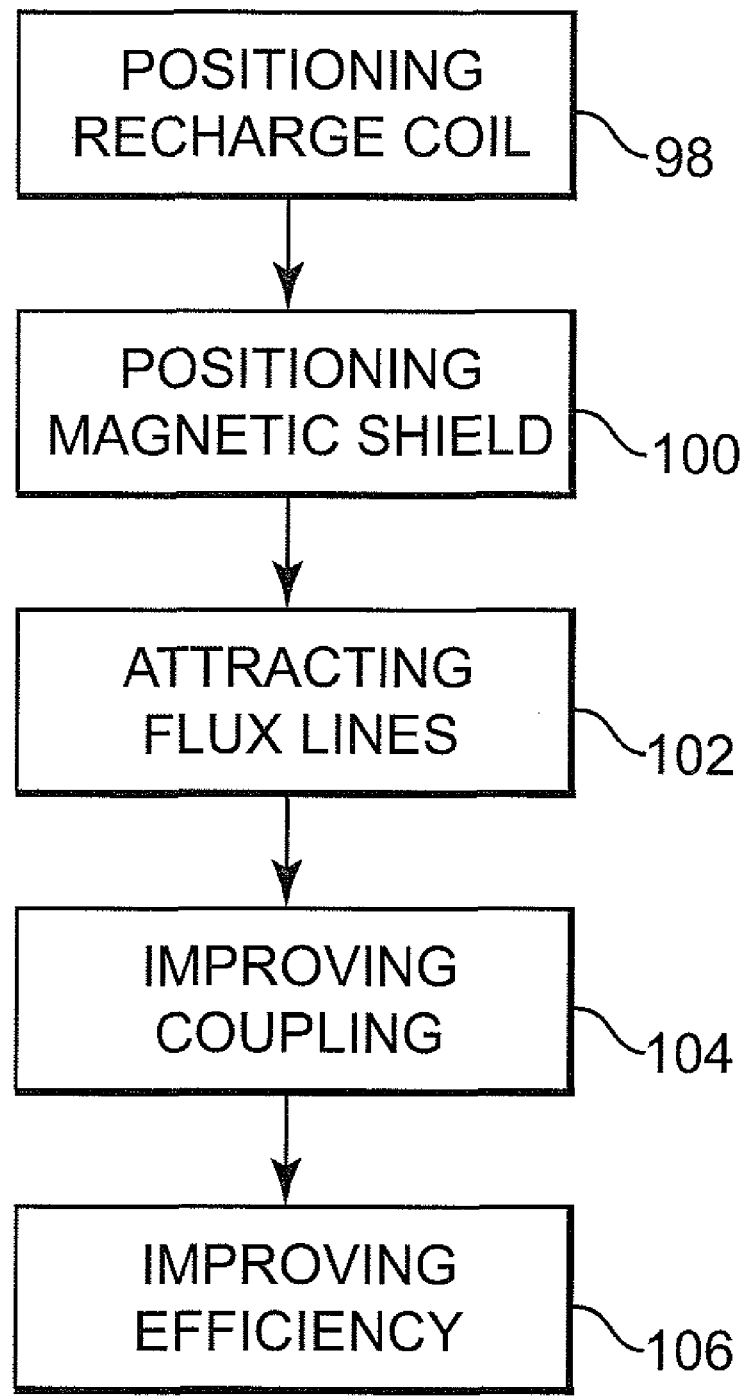
FIG. 11 shows a flowchart of a method for enhancing electromagnetic coupling of an implantable medical device with recharge coil embodiment.

FIG. 11 shows a method for enhancing electromagnetic coupling of an implantable medical device external recharging coil embodiment. Positioning a secondary recharging coil 98 in operational relationship to an implantable medical device 20. Positioning a magnetic shield 100 on the distal side of the secondary recharging coil 68. Attracting electromagnetic flux lines 102 from a primary recharging coil 34 to the secondary recharging coil 68 with the magnetic shield 70. Improving electromagnetic coupling between a primary recharging coil 34 and a secondary recharging coil 68. The improved electromagnetic coupling 104 between the primary recharging coil 34 and the secondary recharging coil 68 is in the range from about 10% to 28% coupling efficiency at about one centimeter. Improving efficiency 106 of energy transfer from the primary recharging coil 34 to the secondary recharging coil 68. The efficiency of energy transfer is improved because less energy is lost to eddy currents in the housing 66.

Figure 12:
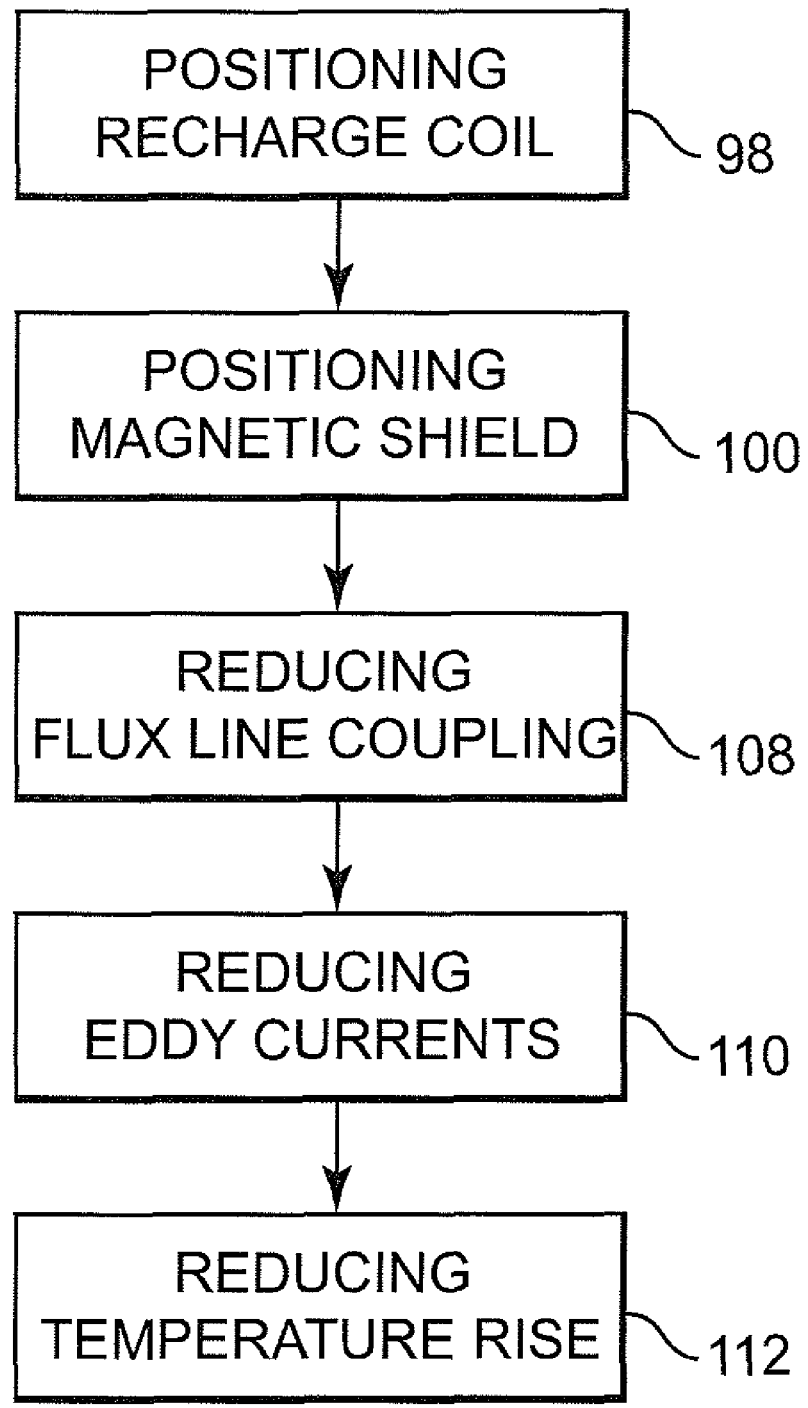
FIG. 12 shows a flowchart of a method for reducing temperature rise of an implantable medical device with recharging coil embodiment.

FIG. 12 shows a method for method for enhancing electromagnetic coupling of an implantable medical device external recharge coil embodiment. Positioning a secondary recharging coil 98 in operational relationship to an implantable medical device 20. Positioning a magnetic shield 100 on the distal side of the secondary recharging coil 68. Reducing electromagnetic flux lines 108 that couple with the housing 66, or electronics 40 carried within the housing 66, or both the housing 66 and electronics 40. Reducing eddy currents 110 in the housing 66 caused by electromagnetic flux lines that couple with the housing 66, or eddy currents in the electronics 40 carried within the housing 66, or both the housing 66 and electronics 40. Reducing temperature rise 112 during recharging because of reduced eddy currents in the housing 66. The implantable medical device 20 temperature rise during recharging is typically controlled to less than about two degrees Centigrade above surround tissue temperature.

Thus, embodiments of an implantable medical device 20 with a recharging coil magnetic shield 70 are disclosed to improve recharging efficiency and many other advantages apparent from the claims. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of coupling electromagnetic flux from a primary charging coil, comprising the steps of:
    operatively coupling a secondary charging coil to an implantable medical device, said secondary charging coil having an axis, a first side and a second side opposite the first side;
    positioning a magnetic shield between the secondary charging coil and the implantable medical device only on the first side of the secondary charging coil, the magnetic shield being approximately perpendicular to the axis of the secondary charging coil; and
    coupling electromagnetic flux from the primary charging coil from the second side of the secondary charging coil.

2. A method of charging of an implantable medical device with a primary charging coil, comprising the steps of:
    operatively coupling a secondary charging coil to the implantable medical device, said secondary charging coil having an axis, a first side and a second side opposite the first side;
    positioning a magnetic shield between the secondary charging coil and the implantable medical device only on the first side of the secondary charging coil, the shield being approximately perpendicular to the axis of the secondary charging coil; and
    applying electromagnetic flux from the primary charging coil from the second side of the secondary charging coil.

3. The method as in claim 2 wherein said applying step results in reduced electromagnetic flux lines that couple with a housing of the implantable medical device.

4. The method as in claim 2 wherein said applying step results in reduced eddy currents in the housing of the implantable medical device caused by electromagnetic flux lines that couple with the housing.

5. The method as in claim 2 wherein a temperature rise induced through eddy currents in the housing during charging is reduced.

6. The method as in claim 2 wherein charging efficiency is improved by decreasing flux lines that couple with the housing.

7. The method as in claim 2 wherein charging efficiency is improved through reduced eddy currents in the housing.

8. The method as in claim 2 wherein reduced eddy currents during recharging also reduces medical device temperature rise during charging.

9. The method as in claim 8 wherein the temperature rise of the implantable medical device during charging is less than two degrees Celsius.

10. The method as in claim 2 wherein the magnetic shield is a material with high magnetic permeability.

11. The method as in claim 10 further comprising the step of selecting the magnetic shield from the group consisting of: amorphous metal film, amorphous metal wire, and magnetic alloy.

12. The method as in claim 2 wherein the medical device is selected from the group consisting of: neuro stimulators, pacemakers, defibrillators, drug delivery pumps, diagnostic recorders, and cochlear implants.

* * * * *